United States Patent
Sims et al.

(10) Patent No.: US 10,429,361 B2
(45) Date of Patent: Oct. 1, 2019

(54) VALVE AND SPLITTING SYSTEM FOR MULTI-DIMENSIONAL LIQUID ANALYSIS

(71) Applicant: Regents of the University of Minnesota, Minneapolis, MN (US)

(72) Inventors: Carl W. Sims, Santa Rosa, CA (US); Peter W. Carr, St. Paul, MN (US); Marcelo Roberto Filgueira, Downingtown, PA (US); Klaus Witt, Keltern (DE)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/996,784

(22) Filed: Jan. 15, 2016

(65) Prior Publication Data
US 2016/0131619 A1     May 12, 2016

Related U.S. Application Data

(63) Continuation of application No. 13/422,168, filed on Mar. 16, 2012, now Pat. No. 9,239,319.
(Continued)

(51) Int. Cl.
*G01N 30/46* (2006.01)
*G01N 30/32* (2006.01)
(Continued)

(52) U.S. Cl.
CPC ........... *G01N 30/463* (2013.01); *G01N 30/10* (2013.01); *G01N 30/32* (2013.01); *G01N 30/465* (2013.01);
(Continued)

(58) Field of Classification Search
CPC .... G01N 30/463; G01N 30/465; G01N 30/10; G01N 30/32; G01N 30/7233; G01N 2030/324
See application file for complete search history.

(56) References Cited

U.S. PATENT DOCUMENTS

| | | | |
|---|---|---|---|
| 5,305,982 A | | 4/1994 | Tamari |
| 5,607,581 A | * | 3/1997 | Gerner .................. G01N 30/36 210/188 |

(Continued)

FOREIGN PATENT DOCUMENTS

| | | |
|---|---|---|
| CN | 101169393 A | 4/2008 |
| CN | 101469015 A | 7/2009 |

(Continued)

OTHER PUBLICATIONS

Murphy et al. ("Effect of Sampling Rate on Resolution in Comprehensive Two-Dimensional Liquid Chromatography", Analytical Chemistry, vol. 70, No. 8, Apr. 15, 1998, see attached publication).*

(Continued)

*Primary Examiner* — Xin Y Zhong
(74) *Attorney, Agent, or Firm* — Shumaker & Sieffert, P.A.

(57) ABSTRACT

A multi-dimensional liquid analysis system includes a flow splitter for separating mobile phase outflow from a first dimension liquid analysis system into first and second liquid split outlet flows. Volumetric flow rate control of the split outlet flows is provided by a flow control pump which withdraws one of the split outlet flows from the flow splitter at a controlled withdrawal flow rate to define the other split outlet flow rate as the difference between the outflow rate from the first dimension system and the withdrawal flow rate. In this manner, accurate and consistent flow division can be accomplished, which is particularly useful for multi-dimensional liquid analysis.

20 Claims, 6 Drawing Sheets

Related U.S. Application Data (60) Provisional application No. 61/466,739, filed on Mar. 23, 2011.

(51) Int. Cl.
  *G01N 30/10* (2006.01)
  *G01N 30/72* (2006.01)

(52) U.S. Cl.
  CPC ... *G01N 30/7233* (2013.01); *G01N 2030/324* (2013.01)

(56) References Cited

U.S. PATENT DOCUMENTS

| | | | |
|---|---|---|---|
| 5,738,783 A | | 4/1998 | Shirota et al. |
| 6,139,734 A | * | 10/2000 | Settlage ............... H01J 49/04 210/198.2 |
| 6,183,635 B1 | | 2/2001 | Klee et al. |
| 6,289,914 B1 | | 9/2001 | Tommasi |
| 6,358,692 B1 | | 3/2002 | Jindal et al. |
| 6,730,228 B2 | * | 5/2004 | Petro ............... B01D 15/1878 210/143 |
| 6,802,967 B2 | | 10/2004 | Masuda et al. |
| 6,855,258 B2 | | 2/2005 | Petro et al. |
| 6,858,435 B2 | | 2/2005 | Chervet et al. |
| 6,989,100 B2 | | 1/2006 | Norton |
| 6,989,129 B2 | | 1/2006 | Licklider et al. |
| 7,111,494 B2 | | 9/2006 | Tipler |
| 7,507,337 B2 | | 3/2009 | Petro et al. |
| 7,624,626 B2 | | 12/2009 | Lee |
| 7,797,988 B2 | | 9/2010 | Schultz et al. |
| 7,900,504 B2 | | 3/2011 | Huynh et al. |
| 7,927,477 B2 | | 4/2011 | Paul et al. |
| 8,115,930 B2 | | 2/2012 | Anderson et al. |
| 8,123,496 B2 | | 2/2012 | Ishii et al. |
| 8,297,107 B2 | | 10/2012 | Tipler et al. |
| 8,621,915 B2 | | 1/2014 | Liu |
| 9,239,319 B2 | | 1/2016 | Sims |
| 2002/0146349 A1 | | 10/2002 | Gygi et al. |
| 2003/0159742 A1 | | 8/2003 | Karp |
| 2005/0214130 A1 | | 9/2005 | Yang |
| 2006/0069418 A1 | | 3/2006 | Schock et al. |
| 2006/0157647 A1 | | 7/2006 | Siuzdak et al. |
| 2007/0199874 A1 | | 8/2007 | Ito et al. |
| 2008/0135484 A1 | | 6/2008 | Hammer et al. |
| 2008/0314129 A1 | * | 12/2008 | Schultz ............... G01N 30/80 73/61.55 |
| 2009/0090174 A1 | | 4/2009 | Paul et al. |
| 2010/0011888 A1 | | 1/2010 | Pawliszyn et al. |
| 2010/0012497 A1 | | 1/2010 | Neyer et al. |
| 2010/0238444 A1 | | 9/2010 | Anderson et al. |
| 2010/0288027 A1 | | 11/2010 | Ishii et al. |
| 2012/0240666 A1 | | 9/2012 | Sims |

FOREIGN PATENT DOCUMENTS

| | | |
|---|---|---|
| EP | 495255 | 7/1992 |
| EP | 0495255 A1 | 7/1992 |
| WO | 2008150763 A1 | 12/2008 |

OTHER PUBLICATIONS

Cacciola et al., "Employing ultra high pressure liquid chromatography as the second dimension in a comprehensive two-dimensional system for analysis of Stevia rebaudiana extracts," Journal of Chromatography A, vol. 1218, Sep. 9, 2010, pp. 2012-2018.

Davis et al., "Effect of First-Dimension Undersampling on Effective Peak Capacity in Comprehensive Two-Dimensional Separations," Analytical Chemistry, vol. 80, No. 2, Jan. 15, 2008, pp. 461-473.

Dugo et al., "Comprehensive Two-Dimensional Normal-Phase (Adsorption)—Reversed-Phase Liquid Chromatography," Analytical Chemistry, vol. 76, No. 9, May 1, 2004, pp. 2525-2530.

Eeltink et al., "Maximizing the Peak Production Rate in Off-line Comprehensive Two-dimensional Liquid Chromatography with Mass Spectrometry Detection," LC GC Europe, Sep. 2009, pp. 404-413.

European Extended Search Report for corresponding European Application No. 12761517.7, 11 pages, dated Aug. 26, 2014.

Filgueira et al., "Improving Peak Capacity in Fast Online comprehensive Two-Dimensional Liquid Chromatography with Post-First-Dimension Flow Splitting", Analytical Chemistry 83, 9531-9539 (2011).

Francois et al., "Comprehensive two-dimensional liquid chromatography applying two parallel columns in the second dimension," Journal of Chromatography A, vol. 1178, Nov. 17, 2007, pp. 33-42.

Giddings, "Two-Dimensional Separations," Analytical Chemistry, vol. 56, No. 12, Oct. 1984, 9 pp.

Groskreutz et al., "Selective comprehensive multi-dimensional separation for resolution enhancement in high performance liquid chromatography. Part I: Principles and instrumentation," Journal of Chromatography A, vol. 1228, Jun. 17, 2011, 31-40, 41-50 pp.

Wei et al., "A comprehensive two-dimensional normal-phase × reversed-phase liquid chromatography based on the modification of mobile phases," Journal of Chromatography A, vol. 1216, Aug. 14, 2009, pp. 7466-7471.

Gu et al., "Effect of first dimension phase selectivity in online comprehensive two dimensional liquid chromatography (LC × LC)," Journal of Chromatography A, vol. 1218, Jul. 24, 2011, pp. 6675-6687.

Guiochon et al., "Implementations of two-dimensional liquid chromatography," Journal of Chromatography A, vol. 1189, Feb. 2008, pp. 109-168.

Horie et al., "Calculating Optimal Modulation Periods to Maximize the Peak Capacity in Two-Dimensional HPLC," Analytical Chemistry, vol. 79, No. 10, May 15, 2007, pp. 3764-3770.

Horvath et al., "Detection issues in two-dimensional on-line chromatography," Journal of Chromatography A, vol. 1216, Sep. 19, 2009, pp. 7785-7792.

Horvath et al., "Generation and Limitations of Peak Capacity in Online Two-Dimensional Liquid Chromatography," Analytical Chemistry, vol. 81, No. 10, May 15, 2009, pp. 3879-3888.

Horvath et al., "Optimization strategies for off-line two-dimensional liquid chromatography," Journal of chromatography A, vol. 1216, Jan. 24, 2009, pp. 2511-2518.

Huang et al., "An experimental study of sampling time effects on the resolving power of on-line two-dimensional high performance liquid chromatography," Journal of Chromatography A, vol. 1218, Apr. 12, 2011, pp. 2984-2994.

Jandera et al., "Effects of the gradient profile, sample volume and solvent on the separation in very fast gradients, with special attention to the second-dimension gradient in comprehensive two-dimensional liquid chromatography," Journal of Chromatography A, vol. 1218, Oct. 30, 2010, pp. 1995-2006.

Kimura et al., "Simple 2D-HPLC using a monolothic silica column for peptide separation," J. Sep. Sci, vol. 27, May 6, 2004, pp. 897-904.

Wang et al., "Peak Capacity Optimization of Peptide Separations in Reversed-Phase Gradient Elution Chromatography: Fixed Column Format," Analytical Chemistry, vol. 78, No. 10, May 15, 2006, pp. 3406-3416.

Li et al., "Equation for Peak Capacity Estimation in Two-Dimensional Liquid Chromatography," Analytical Chemistry, vol. 81, No. 2, Jan. 15, 2009, pp. 845-850.

Liu et al., "Comprehensive Two-Dimensional Gas Chromatography using an On-Column Thermal Modulator Interface," Journal of Chromatographic Science, vol. 29, Jun. 1991, pp. 227-231.

MacNair et al., "Ultrahigh-Pressure Reversed-Phase Liquid Chromatography in Packed Capillary Columns," Analytical Chemistry, vol. 69, No. 6, Mar. 15, 1997, pp. 983-989.

Marchetti et al., "Comprehensive Off-Line, Two-Dimensional Liquid Chromatography. Application to the Separation of Peptide Digests," Analytical Chemistry, vol. 80, No. 8, Apr. 15, 2008, pp. 2756-2767.

Motokawa et al., "Monolithic silica columns with various skeleton sizes andthrough-gore sizes for capillary liquid chromatography", Journal of ChromatographyA, 96 (2002) 53-63.

(56) References Cited

OTHER PUBLICATIONS

Murphy et al., "Effect of Sampling Rate on Resolution in Comprehensive Two-Dimensional Liquid Chromatography", Anal. Chem. 70, 1585-1594 (1998).
Murphy et al., "Effect of Sampling Rate on Resolution in Comprehensive Two-Dimensional Liquid Chromatography," Analytical Chemistry, vol. 70, No. 8, Apr. 15, 1998, pp. 1585-1594.
Office Action from U.S. Appl. No. 14/023,133, dated Jul. 23, 2015, 16 pp.
Potts et al., "The impact of sampling time on peak capacity and analysis speed in online comprehensive two-dimensional liquid chromatography", Journal of Chromatogaphy A, vol. 1217, Jan. 22, 2010, pp. 5700-5709.
Prosecution History from U.S. Appl. No. 13/422,168, dated Aug. 28, 2013 through Aug. 10, 2015, 117 pp.
Schure, "Limit of Detection, Dilution Factors, and Technique Compatibility in Multidimensional Separations Utilizing Chromatography, Capillary Electrophoresis, and Field-Flow Fractionation," Analytical Chemistry, vol. 71, No. 8, Apr. 15, 1999, pp. 1645-1657.
Seeley, "Theoretical study of incomplete sampling of the first dimension in comprehensive two-dimensional chromatography," Journal of Chromatography A, vol. 962, Apr. 9, 2002, pp. 21-27.
Stoll et al., "Fast, comprehensive online two-dimensional high performance liquid chromatography through the use of high temperature ultra-fast gradient elution reversed-phase liquid chromatography," Journal of Chromatography A., vol. 1122, May 23, 2006, pp. 123-137.
Stoll et al., "Fast, comprehensive two-dimensional liquid chromatography," Journal of Chromatography A, vol. 1168, Aug. 30, 2007, pp. 3-43.
Tanaka et al., "Simple and Comprehensive Two-Dimensional Reversed-PhaseHPLC Using Monolitliic Silica columns", Anal. Chem. 2004,76, 1273-1281.
Thompson et al., "Dependence of Thermal Mismatch Broadening on Column Diameter in High-Speed Liquid Chromatography at Elevated Temperatures," Analytical Chemistry, vol. 73, No. 14, Jul. 15, 2001, pp. 3340-3347.

Tranchida et al., "Generation of Improved Gas Linear Velocities in a Comprehensive Two-Dimensional Gas chromatography System," Analytical Chemistry, vol. 79, No. 6, Mar. 15, 2007, pp. 2266-2275.
U.S. Appl. No. 14/023,133, by Marcelo Filgueira, filed Sep. 10, 2013.
Vivo-Truyols et al., "Comprehensive Study on the Optimization of Online Two-Dimensional Liquid Chromatographic Systems Considering Losses in Theoretical Peak Capacity in First- and Second-Dimensions: APareto-Optimality Approach," Analytical Chemistry, vol. 82, No. 20, Oct. 15, 2010, pp. 8525-8536.
First Office Action, and translation thereof, from counterpart Chinese Application No. 201280021822.7, dated Jan. 22, 2016, 22 pp.
Response to Chinese Office Action dated Sep. 26, 2016, from counterpart Chinese application No. 201280021822.7, filed Dec. 12, 2016, 6 pp. (Translation provided for only the claims.).
Second Office Action and Search Report, and translation thereof, from counterpart Chinese Application No. 201280021822.7, dated Sep. 26, 2016, 19 pp.
Third Office Action and Search Report, and translation thereof, from counterpart Chinese Application No. 201280021822.7, dated Mar. 20, 2017, 21 pp.
Response to Examination Report dated Jan. 20, 2017, from counterpart European Application No. 12761517.7, filed May 26, 2017, 10 pp.
Examination Report from counterpart European Application No. 12761517.7-1554, dated Jan. 20, 2017, 5 pp.
Fourth Office Action, and translation thereof, from counterpart Chinese Application No. 201280021822.7, dated Sep. 15, 2017, 13 pp.
Amended Claims, and translation thereof, from counterpart Chinese Application No. 201280021822.7, filed Jun. 5, 2017, 12 pp.
The Notification of Reason for Rejection, and translation thereof, from counterpart Chinese Application No. 201280021822.7, dated Mar. 7, 2018, 15 pp.
Examination Report from counterpart European Application No. 12761517.7, dated Jun. 18, 2019, 4 pp.

\* cited by examiner

VALVE AND SPLITTING SYSTEM FOR MULTI-DIMENSIONAL LIQUID ANALYSIS

This application is a continuation of U.S. application Ser. No. 13/422,168, filed Mar. 16, 2012 and entitled "Valve and Splitting System for Multi-Dimensional Liquid Analysis," which claims the benefit of U.S. Provisional Application No. 61/466,739, filed on Mar. 23, 2011 and entitled "Valve and Splitting System for Two-Dimensional Liquid Chromatography," the entire contents of each being incorporated by reference herein.

GOVERNMENT INTEREST

This invention was made with government support under GM054585 awarded by the National Institutes of Health and CHE-0911330 awarded by the National Science Foundation. The government has certain rights in the invention.

FIELD OF THE INVENTION

The present invention relates to flow systems used in analytical chemistry, and more particularly to a splitting system for splitting mobile phase flow in a multidimensional liquid chromatography apparatus.

BACKGROUND

Separation techniques such as high pressure liquid chromatography (HPLC) are commonly used in analytical chemistry. However, HPLC is limited by the resolution which can be achieved using a single chromatographic separation column. Attempts have been made to combine two or more liquid chromatographs into a hybrid instrument to achieve enhanced resolution of more compounds than can be achieved in a single separation column. As sample complexity has increased over the years, a need has arisen for greater resolving power than that achievable through the use of a single HPLC column.

Some analytical instruments involve the combination of HPLC and mass spectrometry for further identification of the sample. Typical mass spectrometers, however, analyze a significantly lower flow rate than the flow rate typically passed through a HPLC separation column. Analysts have therefore attempted to operate such combined instrumentation by reducing the HPLC mobile phase flow rate to a less than optimum value so that the outflow rate from the HPLC separation matches the liquid flow capacity of the mass spectrometer. Such reduction in flow rate through the HPLC column tends to reduce the available chromatographic resolution. To avoid the reduction in HPLC resolution, flow splitters have been employed in a full-flow regime to split a portion of the flow from the outlet of the HPLC column or detector to the inlet of the mass spectrometer, and the balance of the flow to another detector or to waste. Typical commercial flow splitters make use of resistive tubing elements to split the liquid flow into two or more distinct flow streams. Example flow splitters are described in U.S. Pat. No. 6,289,914, and European patent application Publication No. EP 495255A1. Resistive division of liquid flow is difficult to maintain at uniform levels. Factors such as variable viscosity of the mobile phase, temperature, and any variations in the flow path during the analysis may cause the split ratio between the respective flow paths to change. Such variability becomes of particular concern when multiple dimension liquid chromatography is practiced.

One example chromatographic application where mobile phase splitting is desirable is two-dimensional liquid chromatography (or LC*LC), wherein the first dimension HPLC column effluent is introduced into a second dimension HPLC column, with no portion of the first dimension separation not being introduced into the second dimension column for subsequent "second dimension" separation. Those of ordinary skill in the art of HPLC analysis understand the various techniques are known for injecting a sample into a chromatographic column. In many cases, a sample volume is established in a multi-port valve, and thereafter injected into the chromatographic column by a fluid force generated by a pump. Samples may be introduced into a flowing mobile phase stream.

Theoretically, it is desirable to have the entire volume of the first dimension separation injected into the second dimension separation column, though such an approach remains impractical as the rate of the effluent from the first separation column is far too great to be directly injected into the second separation column. Traditionally, therefore, analysis of the "first dimension" separation has been accomplished by collection of the total volume of the effluent from the first separation column by fraction collection, and then re-injecting a representative sample of each fraction into the second dimension separation column.

In addition to flow rate mismatch, the developing chromatogram in the first dimension may contain increasing relative concentrations of organic solvent. The increasing relative concentration of organic solvent may be a result of the particular liquid chromatographic approach, in which an organic solvent is injected into the separation column after an aqueous mobile phase. As the relative concentration of organic solvent increases in the first dimension separation, injection of a fixed volume from the first dimension into the second dimension chromatograph further increases the relative organic solvent concentration during the second dimension separation. Under some conditions, injecting large volumes of organic solvent into the second dimension chromatograph is destructive to the second dimension separation. As the variation in organic solvent versus time occurs in the first dimension separation, the flow rate exiting from standard resistive flow splitters disposed downstream from the first separation column becomes unpredictable. Analysts therefore find it difficult to know the actual flow rate of sample available for injection into the second dimension separation column. An understanding of the sample flow rate is critical to control the organic solvent concentration in the second dimension separation column, and to ensure that no portion of the first dimension chromatograph is unsampled in the second dimension separation. Typical resistive flow splitters are not capable of providing analysts with the necessary information to consistently control analysis in the second dimension. Because of the limitations of standard resistive flow splitters, LC*LC has not enjoyed wide usage in the art.

SUMMARY OF THE INVENTION

A flow splitting system includes a T-style junction having an inlet for receiving fluid exiting a first HPLC system separation column, a first outlet for permitting indirectly flow controlled outflow therefrom, the first outlet being fluidly coupled to a flow restricting device, and a second outlet for permitting directly flow controlled outflow therefrom. The second outlet is fluidly coupled to a positive displacement pump operable in a negative displacement mode or a positive displacement mode. The flow restricting device creates a pressure in the junction from 1 kilopascal to 10,000 kilopascals, and is an adjustable pressure regulator. The system further includes a positive displacement pump and valve system wherein a 3-port shear type valve is used to connect a pump piston and barrel to either the junction or to waste.

In some embodiments, the positive displacement pump is capable of being driven at a constant rate in the negative displacement mode and is capable of withstanding pressure caused by the flow restricting device connected to the first outlet of the junction.

In some embodiments, the positive displacement pump is driven at a variable rate in the negative displacement mode.

In some embodiments, the positive displacement pump is driven at a negative volume displacement rate which is less than the rate of solvent inflow into the junction from the first dimension HPLC system.

In some embodiments, a 6-port sample injection valve for a second dimension HPLC system is placed between the positive displacement pump and the second outlet of the junction.

In some embodiments, a 10-port valve configured as a dual-loop injector for a second dimension HPLC system is placed between the positive displacement pump and the second outlet of the junction.

In some embodiments, the first outlet of the junction is connected to an inlet of a mass spectrometer.

In some embodiments, a draw time in which the positive displacement pump draws sample into the second dimension injection valve is equal to or slightly less or slightly more than an analysis time for a second dimension separation.

In some embodiments, an injection loop volume in the second dimension 6-port injection valve is either partially filled or fully filled during a time of analysis of a previously injected sample and at a rate such that a complete representative sampling of all compounds exiting from the first dimension HPLC system enter a sample loop in the second dimension injection valve.

In some embodiments, injection of the sample contained within the sample loop of the second dimension injection valve takes place within one time standard deviation of any analysis peak in a separation of the sample performed by the first dimension HPLC system separation column.

In some embodiments, the time that the second dimension injection valve remains in an inject position is less than 10 percent of the total analysis time of the second dimension HPLC system separation column.

A flow splitting system for liquid chromatography includes a T-style junction having an inlet for receiving fluid exiting a first HPLC system flow-through detector, a first outlet for permitting indirectly flow controlled outflow therefrom, the first outlet being fluidly coupled to a flow restricting device, and a second outlet for permitting directly controlled outflow therefrom. The second outlet is fluidly coupled to a positive displacement pump operable in a negative displacement mode or a positive displacement mode. The flow restricting device creates a pressure in the junction from 1 kilopascal to 10,000 kilopascals, or the maximum backpressure that said detector can withstand, and the flow restricting device is an adjustable pressure regulator. The system further includes a positive displacement pump and valve system wherein a 3-port shear type valve is used to connect a pump piston and barrel to either the junction or to waste.

In some embodiments, the positive displacement pump is capable of being driven at a constant rate in the negative displacement mode and is capable of withstanding pressure caused by the flow restricting device connected to the first outlet of the junction.

In some embodiments, the positive displacement pump is driven at a negative volume displacement rate which is less than the rate of solvent inflow into the junction from a first dimension HPLC system.

In some embodiments, a 6-port sample injection valve for a second dimension HPLC system fluidly coupled between the positive displacement pump and the second outlet of the junction.

In some embodiments, a 10-port injection valve configured as a dual-loop injector for a second dimension HPLC system is fluidly coupled between the positive displacement pump and the second outlet of the junction.

In some embodiments, the first outlet of the junction is connected to an inlet of a mass spectrometer.

DETAILED DESCRIPTION OF THE PREFERRED EMBODIMENTS

To effectuate consistent splitting of effluent flow from a first dimension analysis column in a manner to preserve the first dimension separation resolution, a positive displacement pump, such as a syringe pump, may be employed in a negative displacement mode to intake fluid at a specific rate from one outlet of a flow splitter. The resultant flow from a second outlet of the flow splitter is also therefore controlled. Such control dictates that the flow rate in both outlets of the split is known.

Figure 1:
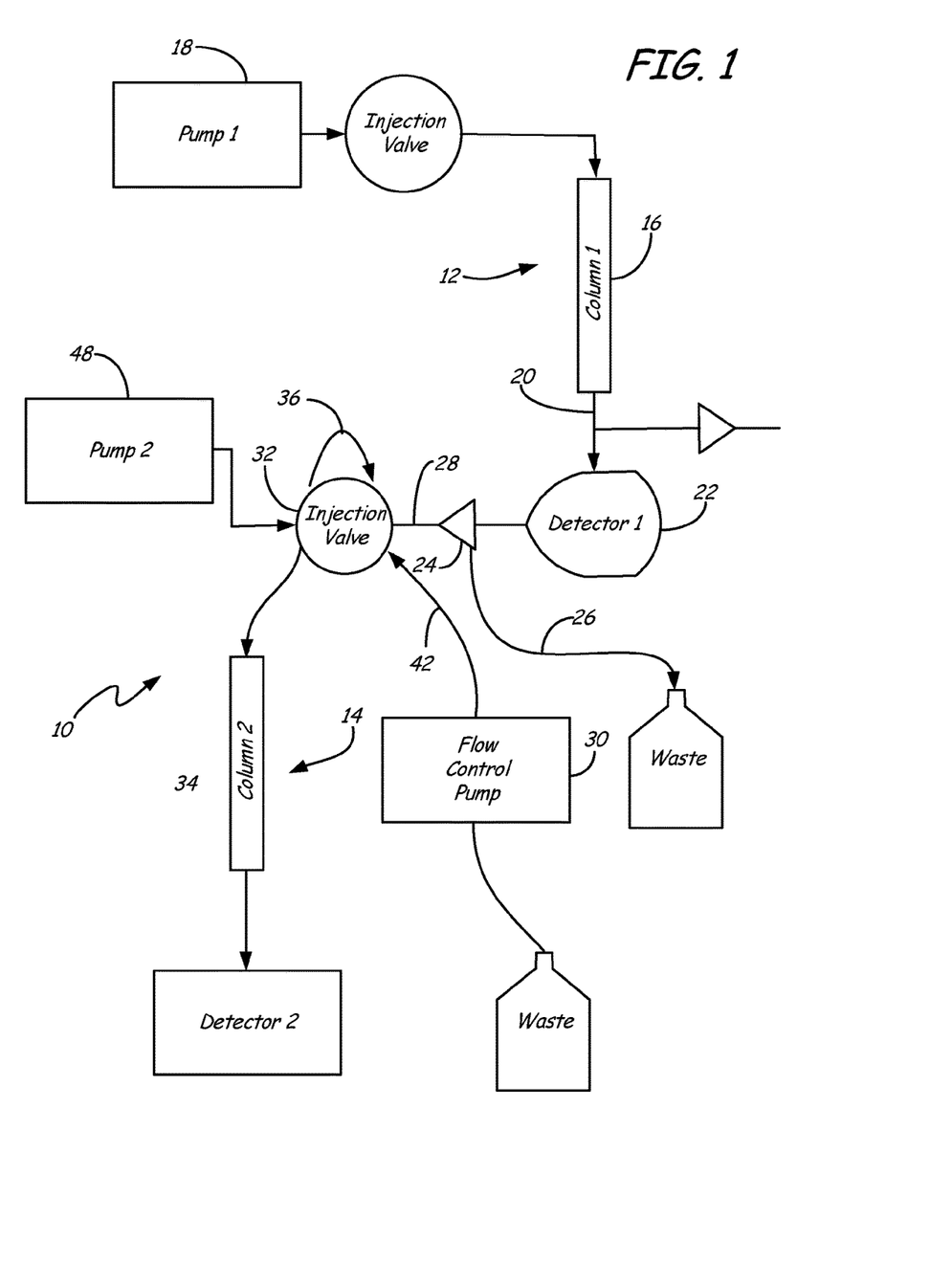
FIG. 1 a schematic view of a system of the present invention.

A first schematic diagram of an arrangement of the present invention is provided in FIG. 1. Analysis system 10 includes a first dimension separation system 12, and a second dimension separation system 14, wherein mobile phase is driven through a first dimension separation column 16 by a first dimension pump 18. First dimension outflow 20 from column 16 may be delivered to a first dimension chromatographic detector 22, or may first be split by a flow splitter. Flow rate into flow splitter 24 is controlled by first dimension pump 18, which defines the flow rate of mobile phase through first dimension column 16. Flow splitter 24 may comprise a T-style junction fitting having a first inlet and first and second outlets, such as that available from Kinesis-USA as a "Micro-Splitter Valve 10-32/6-32 Port 55 Needle (EA)". In the arrangement illustrated in FIG. 1, a first outlet 26 from flow splitter 24 comprises a waste stream, while a second outlet 28 from flow splitter 24 is at least intermittently fluidly coupled to flow control pump 30. In other embodiments, however, first outlet 26 may comprise a flow stream of known flow rate for delivery to a secondary analysis system, such as a mass spectrometer. System 10 is arranged such that first outlet 26 need only have sufficient flow restriction to avoid over-pressurization of pump 30 during the time that pump 30 controls fluid flow through second outlet 28. In such a manner, control is exerted over both first and second outlets 26, 28 of flow splitter 24 through control of the fill rate of pump 30 in a negative displacement mode. Consequently, no additional unswept volume is interposed between flow splitter 24 and any detection means (such as a mass spectrometer) fluidly coupled to first outlet 26.

Analysis system 10 performs chemical analysis of liquid sample pumped into first and second dimension columns 16, 34. For the purposes of this invention, first and second dimension "columns" may be construed broadly, so as to include analysis modalities that do not necessarily involve a column. For example, one or more of the dimensions may involve liquid chromatography, HPLC, preparative-scale liquid chromatography, supercritical fluid analysis, gel permeation chromatography, mass spectrometry, other spectrometry or chromatography analysis, and combinations thereof. In a particular application, the first and second dimensions are each chromatographic columns for evaluating a liquid sample. In some embodiments, such liquid chromatography may be "high pressure liquid chromatography" or "high performance liquid chromatography" (HPLC), which is a common technique for performing chromatographic separations of solutions of compounds delivered to an injection valve or "autosampler" by pump for injection into the chromatographic separation column. Liquids and liquid mixtures used to transport the compounds are referred to herein as the "mobile phase". The "stationary phase" of liquid chromatography is typically the packing materials within the separation columns 16, 34.

As indicated above, flow control pump 30 may typically be a positive displacement pump having a displacement volume that is filled in a negative displacement mode, and discharged in a positive displacement mode. An example positive displacement pump is a syringe pump, in which a plunger within a cylinder acts in a negative displacement mode to draw liquid into the cylinder through controlled withdrawal of the plunger that creates a negative pressure within the cylinder to draw liquid therein. Movement of the plunger in an opposite direction establishes a "positive displacement mode", wherein a positive pressure is created in the cylinder, so that the contents of the cylinder are discharged therefrom.

Flow control pump 30 may be placed downstream of any valve in second outlet stream 28, such that splitting of outflow 20 may be precisely controlled at known rates by controlling the rate at which pump 30 draws fluid through second outlet stream 28. So long as the second outlet stream 28 does not exceed the total flow rate at outlet flow 20, flow volume versus time is known precisely in both first and second outlet streams 26, 28.

Figure 2:
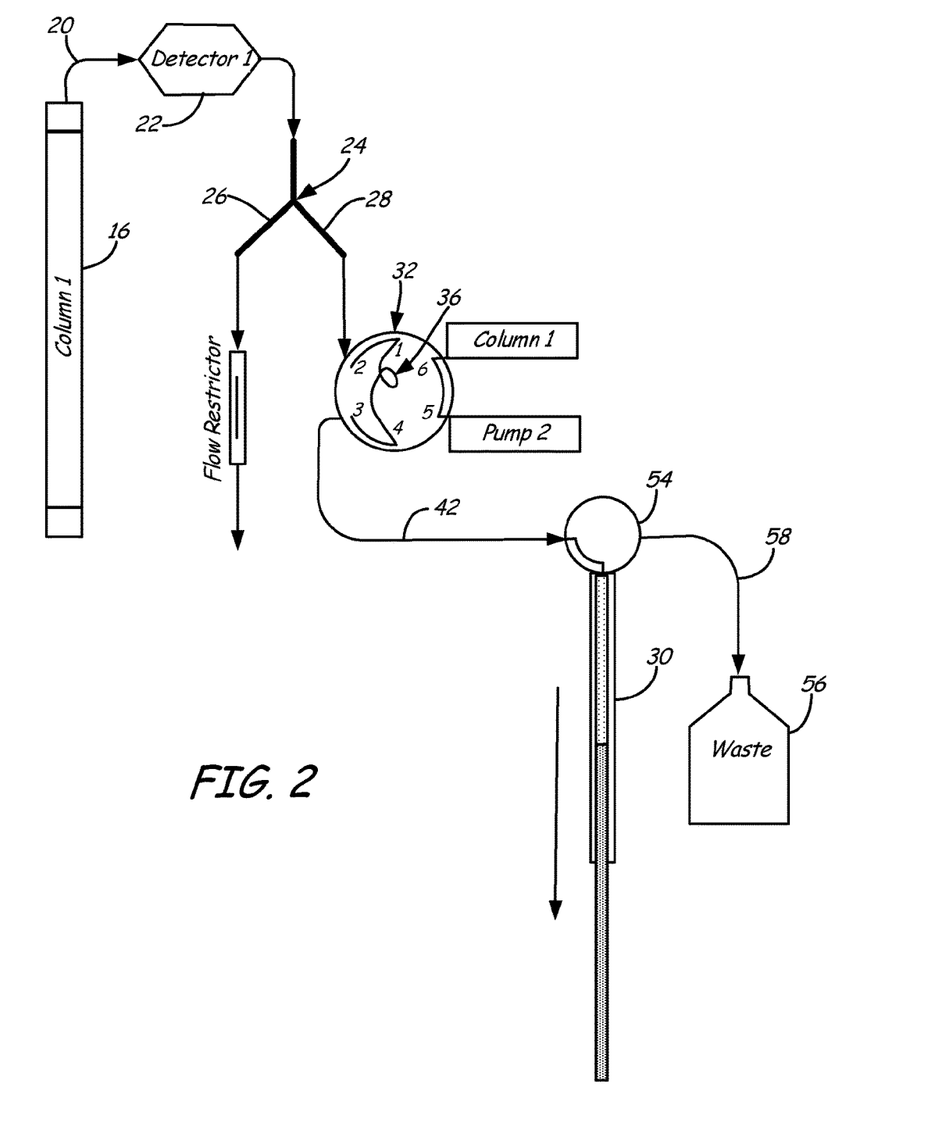
FIG. 2 a schematic view of a system of the present invention.

In the embodiment illustrated in FIG. 1, splitter 24 may be positioned between an outlet of first dimension column 16 and a second dimension injection valve 32. Depending upon the maximum volume of the first dimension mobile phase from outlet 20 to be injected into second dimension separation column 34, a fixed volume sample loop 36 of such maximum volume may be incorporated with the second dimension injection valve 32 in the form of a tube, channel, or other vessel capable of temporarily containing the volume of sample mobile phase. Sample loop 36 is more clearly illustrated in FIG. 2, with second dimension injection valve 32 being a 6-port injection valve, as is known in the art. In this embodiment, sample loop 36 has a volume that is equal to or greater than the desired sample volume deliverable to the second dimension column 34. The programmed flow rate of pump 30 may be substantially equal to such sample volume divided by the analysis time required of the second dimension column 34. Such calculated withdrawal flow rate of flow stream 42 ensures that a representative sample of all mobile phase passing through flow splitter 24 is delivered to second dimension column 34. The following sets forth a relationship for an example control scheme for pump 30 to establish an appropriate withdrawal flow rate from first dimension outflow 20, and to therefore retain a sufficient second dimension sample delivery flow rate to ensure complete chromatographic analysis of mobile phase in second outlet stream 28:

$$F_c \leq V_L/(T_{2a}+T_{2e})$$

Wherein,
$F_c$=controlled flow rate at pump flow stream 42
$V_L$=volume of sample loop 36
$T_{2a}$=analysis time of second dimension column 34
$T_{2e}$=equilibration time of second dimension The "equilibration time" of the second dimension is the time required to "flush" the second dimension column of an opposite-phase solvent. For example, certain HPLC analyses are performed by first passing an aqueous phase through the column, followed by an organic phase, with the sample being injected as appropriate into one or both of the aqueous/organic phases. The sample is eluted through the chromatographic column through the sequence of alternating aqueous/organic phases. Once the sample has finished eluting through the chromatographic column, it is desired that the column be "cleared" of any remaining aqueous/organic phase that is opposite to the initial mobile phase in the subsequent sample analysis. Therefore, in the example of a sample tested with first an aqueous phase, followed by an organic phase, such organic phase is preferably "flushed" from the column with blank aqueous phase (such as water) prior to initiating the subsequent sample sequence. This "flushing" time is the "equilibration time" utilized in the above relationship.

Figure 3:
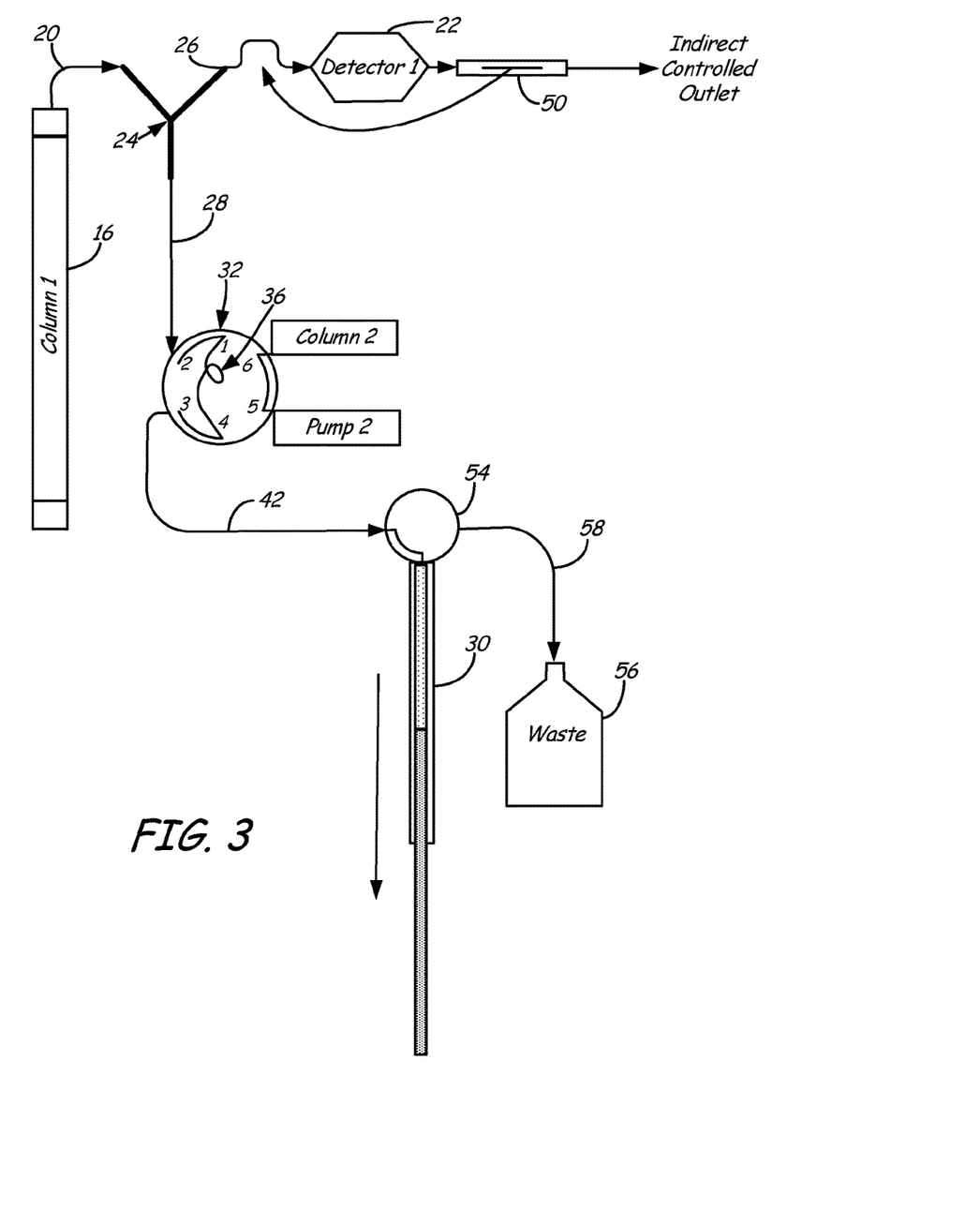
FIG. 3 a schematic view of a system of the present invention.

An alternative embodiment is illustrated in FIG. 3, wherein first dimension detector 22 is positioned downstream of flow splitter 24 in fluid communication with first outlet stream 26. A flow restrictor 50 may be employed downstream of detector 22, or between splitter 24 and first dimension detector 22, in order to provide sufficient flow restriction to enable pump 30 to operably control flow division at splitter 24. Positioning flow restrictor 50 upstream of first dimension detector 22 may eliminate back pressure applied to detector 22 to improve sampling accuracy. In any case, however, flow restrictor 50 is optionally included, and is not necessary for the operation of the present invention.

Figure 4:
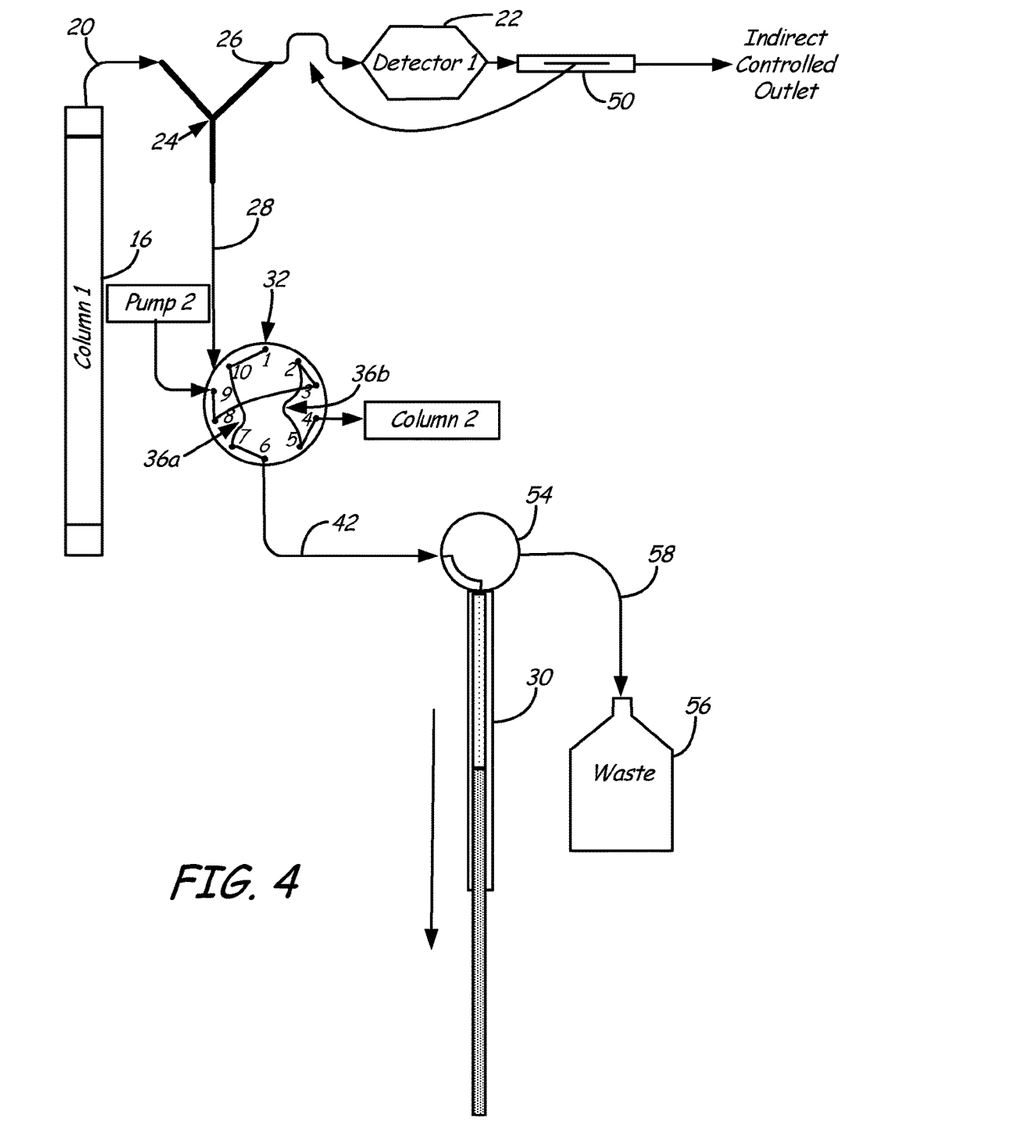
FIG. 4 a schematic view of a system of the present invention.
Figure 5:
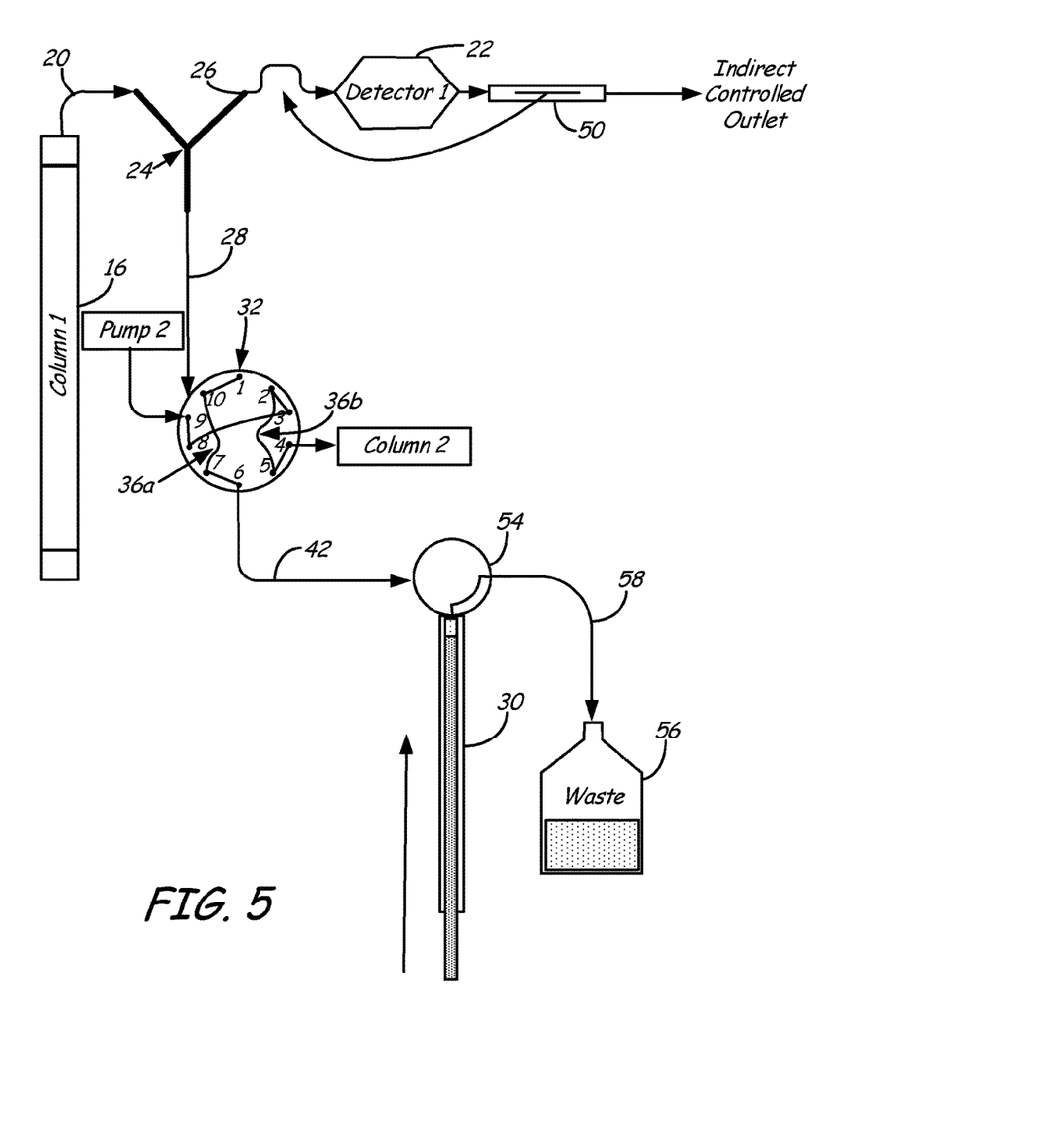
FIG. 5 a schematic view of a system of the present invention.

A further embodiment of the invention is illustrated in FIGS. 4 and 5, wherein second dimension injection valve 32 is a 10-port valve, as is known in the art. In such embodiment, two distinct flow paths may be established for use as a double loop injector. In a first flow path, sample may be directed through a first sample loop 36a directly, while in a second flow path, sample may be directed through a second sample loop 36b on valve 32. The difference in flow paths and the difference in resistance to flow is negated when using a flow splitter driven by a pump 30 as described herein. First sample loop 36a may be filled while the sample within second sample loop 36b is analyzed in second dimension column 34. In this case, pump 30 may be operated in a negative displacement mode to draw mobile phase from first dimension outlet stream 20 sequentially into each of first and second sample loops 36a, 36b. The draw rate through second outlet 28 may be such that the sample loop volume being filled represents a volume suitable to be consumed over the entire time of the analysis and the equilibration of the second dimension analysis ($T_{2a}+T_{2e}$). First and second sample loops 36a, 36b may be alternately filled and injected to second dimension column 34. An advantage of this technique is that each sample loop 36a, 36b is fully washed by the mobile phase of the second dimension over the entire time of analysis to eliminate carryover.

Figure 6:
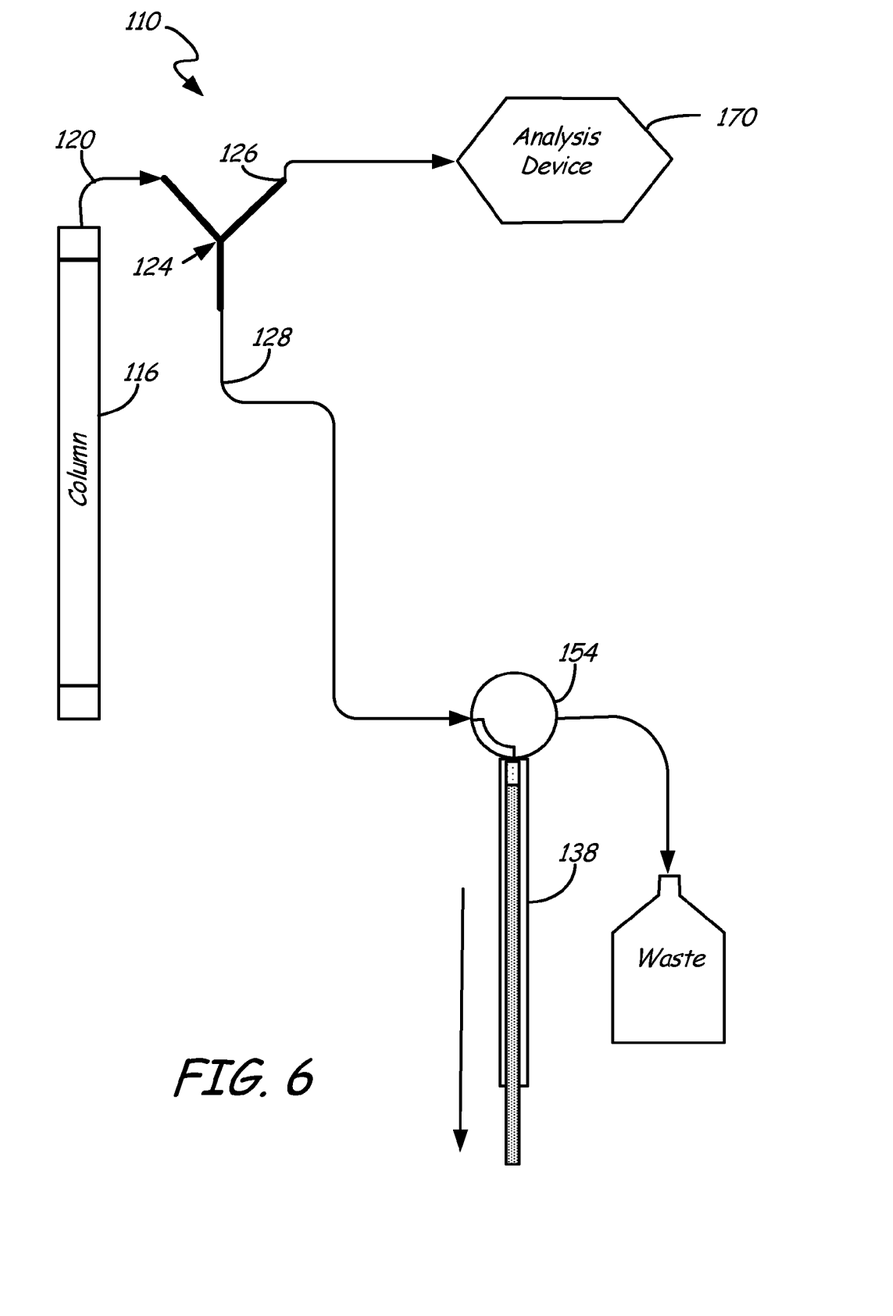
FIG. 6 a schematic view of a system of the present invention.

A waste discharge cycle of pump 30 is illustrated in FIG. 5. A valve 54 may be employed to alternate between intake of mobile phase through flow stream 42 (as shown in FIGS. 2-4) and discharge to waste 56 through waste flow line 58 (as shown in FIGS. 5 and 6). In one embodiment, syringe pump 30 may be operated in a positive displacement mode to discharge its accumulated contents in a discharge time period ($T_d$) that is less than one standard deviation in time for an analysis peak occurring in the first dimension separation. In this manner, no particular chromatographic analysis peak remains unsampled in the second dimension chromatograph 34. In one embodiment, therefore, discharge time $T_d$ may be less than about 1 second.

Discharge from the pump 30 may occur only at intervals in which the mobile phase substantially fills the displacement volume of pump 30. For example, first and second sample loops 36a, 36b may each be 20 microliters in volume, while syringe pump 30 may have a displacement volume of 5 ml. As a result, the displacement volume of pump 30 may become filled only after 125 injections into the second dimension chromatograph 34.

A further embodiment is illustrated in FIG. 6, wherein system 110 includes a flow splitter 124 disposed downstream from a first dimension column 116. First outlet stream 126 from flow splitter 124 is fluidly coupled to an inlet of a secondary analysis device 170, such as a mass spectrometer. A second outlet stream 128 from flow splitter 124 is fluidly coupled to a pump 130 to control the flow rate division at flow splitter 124. As described above, pump 130 programmably removes solvent from outflow stream 120 at a desired rate, such that the inlet flow rate to secondary analysis device 170 though first outlet stream 126 is equal to outlet flow rate 120 from first dimension column 116, less the flow rate being drawn into pump 130 through second outlet stream 128.

Fluid flow into the head of a liquid chromatographic column is not always the total flow delivered to the inlet of the first dimension pump 18 if the pump 18 is used to mix the mobile phase components, such as in gradient elution chromatography. Such an effect is caused by volumetric shrinkage of mixing, which results in the mixed mobile phase volume being less than the sum of the two individual liquid volumes. To accommodate such volumetric shrinkage of mixing, pump 30, 130 may be programmed according to the concentration of individual components of the mobile phase. An example relationship for such pump programming may be as follows:

$$F_i = k * F_o$$

Wherein:
$F_i$=indirect flow rate
k=volumetric shrinkage factor
$F_o$=flow rate at outlet 120

Although an HPLC pump delivers a constant flow of each individual solvent to a mixing point, the total flow rate from the mixing point may be different from the sum of the individual liquid flows. As such, flow into an HPLC column may be greater than the flow rate out of the HPLC column when temperature is constant. The pump 30, 130 may therefore be adjusted to accommodate a difference between the inlet and outlet flow rates. Moreover, if the first dimension HPLC column 16, 116 is heated, the use of a pressurized, negative displacement flow splitter permits all points of the second outlet stream 28, 128 to be pressurized such that boiling or outgassing of the mobile phase will not cause intermittent flow. In fact, when a first dimension column 16, 116 is heated, the use of negative displacement flow splitting may be the only effective method for loading the sample loop of the injector without boiling of the solvent.

What is claimed is:

1. A multi-dimensional liquid analysis system, comprising:
   a first separation system including a first separation column, the first separation column configured to chromatographically separate a sample within a liquid mobile phase and to provide a first dimension outflow having a first outflow rate;
   a flow splitter fluidly coupled to the first dimension outflow, the flow splitter configured to split the first dimension outflow into a first split outlet flow and a second split outlet flow;
   a second separation system including a sample loop and a second separation column, wherein the second separation system is configured that the sample loop receives a sample volume from the second split outlet flow, and wherein the second separation column is configured to chromatographically separate the sample volume from the second split outlet flow; and
   a flow control pump fluidly coupled to and located downstream of one of the first split outlet flow and the second split outlet flow, the flow control pump configured to withdraw the one of the first split outlet flow and the second split outlet flow from the flow splitter at a controlled withdrawal flow rate to obtain, in the sample volume from the second split outlet flow, a representative sampling of compounds in the first dimension outflow for separation in the second separation system.

2. The multi-dimensional liquid analysis system of claim 1, further comprising:
   a flow restrictor restricting the first split outlet flow to create a fluid pressure at the flow splitter of 1-1000 kilopascals.

3. The multi-dimensional liquid analysis system of claim 1,
   wherein the flow control pump is a positive displacement pump configured to withdraw the one of the first split outlet flow and the second split outlet flow from the flow splitter at the controlled withdrawal flow rate while operating in a negative displacement mode.

4. The multi-dimensional liquid analysis system of claim 1, wherein the controlled withdrawal flow rate is controlled according to:

$$F_c \leq \frac{V_s}{(T_{2a} + T_{2e})},$$

wherein:
$F_c$ is the flow rate for the second split outlet flow, $V_s \geq V_d$, $V_d$ is a volume of the second split outlet flow to be analyzed by the second separation column, $T_{2a}$ is an analysis time of the second separation column, and $T_{2e}$ is an equilibration time of the second separation column.

5. The multi-dimensional liquid analysis system of claim 1, further comprising:
a multiple-port injection valve configured to inject the sample volume from the second split outlet flow into the second separation column.

6. The multi-dimensional liquid analysis system of claim 5, wherein to control the flow rate of the one of the first split outlet flow and the second split outlet flow from the flow splitter, the flow control pump is configured to produce a flow rate for the second split outlet flow that is controlled according to:

$$F_c \le \frac{V_L}{(T_{2a} + T_{2e})},$$

wherein:
$F_c$ is the flow rate for the second split outlet flow,
$V_L$ is a volume of the sample loop,
$T_{2a}$ is an analysis time of the second separation column, and
$T_{2e}$ is an equilibration time of the second separation column.

7. A multi-dimensional liquid analysis system, comprising:
a first separation system including a first separation column, the first separation column configured to chromatographically separate a sample within a liquid mobile phase and to provide a liquid mobile phase into a first dimension outflow having a first outflow rate;
a flow splitter fluidly coupled to the first dimension outflow, the flow splitter configured to split the first dimension outflow into a first split outlet flow and a second split outlet flow;
a second separation system including a multiple-port injection valve comprising a sample loop, the second separation system also including a second separation column, wherein the multiple-port injection valve is configured to receive, at a port, the second split outlet flow such that the sample loop receives a sample volume from the second split outlet flow, and wherein the second separation column is configured to chromatographically separate the sample volume from the second split outlet flow; and
a flow control pump fluidly coupled to and located downstream of one of the first split outlet flow and the second split outlet flow, the flow control pump configured to withdraw the one of the first split outlet flow and the second split outlet flow from the flow splitter at a controlled withdrawal flow rate to obtain, in the sample volume from the second split outlet flow, a representative sampling of compounds in the first dimension outflow for separation in the second separation system.

8. The multi-dimensional liquid analysis system of claim 7, further comprising:
a flow restrictor restricting the first split outlet low to create a fluid pressure at the flow splitter of 1-1000 kilopascals.

9. The multi-dimensional liquid analysis system of claim 7, wherein the flow control pump comprises a positive displacement pump configured to withdraw the one of the first split outlet flow and the second split outlet flow from the flow splitter while operating in a negative displacement mode.

10. The multi-dimensional liquid analysis system of claim 7, wherein the controlled withdrawal flow rate is controlled according to:

$$F_c \le \frac{V_s}{(T_{2a} + T_{2e})},$$

wherein:
$F_c$ is the flow rate for the second split outlet flow, $V_s \ge V_d$, $V_d$ is a volume of the second split outlet flow to be analyzed by the second separation column,
$T_{2a}$ is an analysis time of the second separation column, and
$T_{2e}$ is an equilibration time of the second separation column.

11. The multi-dimensional liquid analysis system of claim 7,
wherein the multiple-port injection valve is configured to inject the sample volume from the second split outlet flow into the second separation column.

12. The multi-dimensional liquid analysis system of claim 11, wherein the controlled withdrawal flow rate is controlled according to:

$$F_c \le \frac{V_L}{(T_{2a} + T_{2e})},$$

wherein:
$F_c$ is the flow rate for the second split outlet flow,
$V_L$ is a volume of the sample loop,
$T_{2a}$ is an analysis time of the second separation column, and
$T_{2e}$ is an equilibration time of the second separation column.

13. A method of multi-dimensional liquid analysis, comprising:
chromatographically separating, using a first separation column, a sample within a liquid mobile phase and providing, from the first separation column, a first dimension outflow having a first outflow rate;
splitting, with a flow splitter having an inlet fluidly coupled to the first dimension outflow, the first dimension outflow into a first split outlet flow and a second split outlet flow;
withdrawing, with a flow control pump fluidly coupled to and located downstream of one of the first split outlet flow and the second split outlet flow, the one of the first split outlet flow and the second split outlet flow from the flow splitter at a controlled withdrawal flow rate to obtain, in a sample volume from the second split outlet flow, a representative sampling of compounds in the first dimension outflow for separation in a second separation system;
receiving, with a sample loop, the sample volume from the second split outlet flow; and chromatographically separating, using a second separation column, the sample volume from the second split outlet flow.

14. The method of claim 13, further comprising:
modifying, without modifying the first outflow rate of the first dimension outflow, the flow rate of the one of the first split outlet flow and the second split outlet flow from the flow splitter by reconfiguring the flow control pump.

15. The method of claim 13, further comprising:
restricting, with a flow restrictor, the first split outlet flow to create a fluid pressure at the flow splitter of 1-1000 kilopascals.

16. The method of claim 13, wherein the flow control pump is a positive displacement pump, the method further comprising:
configuring the flow control pump in a negative displacement mode to withdraw the one of the first split outlet flow and the second split outlet flow from the flow splitter at the controlled withdrawal flow rate.

17. The method of claim 13, further comprising:
configuring the flow control pump to produce a flow rate for the second split outlet flow according to:

$$F_c \leq \frac{V_s}{(T_{2a} + T_{2e})},$$

wherein:
$F_c$ is the flow rate for the second split outlet flow, $V_s \geq V_d$, $V_d$ is a volume of the second split outlet flow to be analyzed by the second separation column, $T_{2a}$ is an analysis time of the second separation column, and $T_{2e}$ is an equilibration time of the second separation column.

18. The method of claim 13, further comprising:
configuring a multiple-port injection valve to inject the sample volume from the second split outlet flow into the second separation column.

19. The method of claim 18, further comprising:
configuring the flow control pump to produce a flow rate for the second split outlet flow according to:

$$F_c \leq \frac{V_L}{(T_{2a} + T_{2e})},$$

wherein:
$F_c$ is the flow rate for the second split outlet flow,
$V_L$ is a volume of the sample loop,
$T_{2a}$ is an analysis time of the second separation column, and
$T_{2e}$ is an equilibration time of the second separation column.

20. The method of claim 18, wherein the multiple-port injection valve includes a port configured to receive the second split outlet flow.

* * * * *